United States Patent [19]

Cohnen et al.

[11] 4,446,142

[45] May 1, 1984

[54] SUBSTITUTED OXADIAZOLES AND THIADIAZOLES, AND METHODS OF PREPARATION AND USE THEREOF

[75] Inventors: Erich Cohnen; Ben Armah, both of Hamburg, Fed. Rep. of Germany

[73] Assignee: Beiersdorf Aktiengesellschaft, Fed. Rep. of Germany

[21] Appl. No.: 277,535

[22] Filed: Jun. 26, 1981

[30] Foreign Application Priority Data

Jun. 27, 1980 [DE] Fed. Rep. of Germany ....... 3024187

[51] Int. Cl.$^3$ .............................................. A61K 31/41
[52] U.S. Cl. .................................... 424/269; 548/128; 548/133
[58] Field of Search ................. 548/133, 128; 424/270, 424/272, 269

[56] References Cited

U.S. PATENT DOCUMENTS 2,648,669  8/1953  Roemer et al. ...................... 548/133

FOREIGN PATENT DOCUMENTS 2461882  7/1975  Fed. Rep. of Germany .
1581394  9/1969  France .
47-61190  2/1974  Japan ................................. 548/128

OTHER PUBLICATIONS

Kurzer; J. Chem. Soc. (1956), pp. 2345-2352.
Kurzer; Chem. Abs. vol. 51,3578e, 3579b, (1957).
Kurzer et al.; Chem. Abs. vol. 54; 4550a, (1960).
Kurzer et al.; Chem. Abs. vol. 55; 1588f and 25926e, (1961).
Kurzer; Chem. Abs. vol. 51; 8079a, (1957).
Tilley et al.; Helv. Chem. Acta. vol. 63, pp. 832-840, 841-859, (1980).
Heterocyclic Chemistry, vol. 5, pp. 141-143, (1965).

*Primary Examiner*—Mary C. Lee
*Attorney, Agent, or Firm*—Jordan B. Bierman; Linda Bierman

[57] ABSTRACT

Compounds of the formula

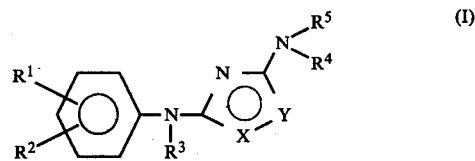

(I)

wherein $R^1$ is hydrogen, halogen, or alkyl, $R^2$ is halogen or alkyl, $R^3$ is hydrogen, acyl, or saturated or unsaturated alkyl, $R^4$ and $R^5$ are individually hydrogen, or alkyl, wherein all alkyl and acyl groups are branched or straight-chain and each contains 1 to 4 carbon atoms, X is oxygen, nitrogen, or sulfur, Y is oxygen or nitrogen, and —X—Y— is —O—N—, —N—O—, or —S—N—, or salts of the above, with certain exceptions. Methods of preparation of the compounds, as well as their use as anti-hypertensives are also disclosed.

23 Claims, No Drawings

SUBSTITUTED OXADIAZOLES AND THIADIAZOLES, AND METHODS OF PREPARATION AND USE THEREOF

This Application claims the priority of German 30 24 187.3, filed June 27, 1980.

The present invention is directed to certain compounds which have been found useful in the treatment of hypertension.

The present invention comprises compounds of the formula

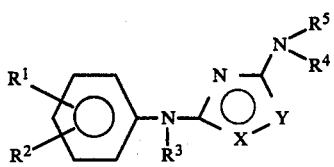

wherein $R^1$ is hydrogen, halogen, or alkyl, $R^2$ is halogen or alkyl, $R^3$ is hydrogen, acyl, or saturated or unsaturated alkyl, $R^4$ and $R^5$ are individually hydrogen or alkyl, wherein said alkyl and said acyl are branched or straight-chain and each contains 1 to 4 carbon atoms, X is oxygen, nitrogen, or sulfur, Y is oxygen or nitrogen and —X—Y— is —O—N—, —N—O—, or —S—N—, and salts thereof, except 3-amino-5-(4-methyl-phenylamino)-1,2,4-oxadiazole
3-(4-methyl-phenylamino)-5-amino-1,2,4-oxadiazole
3-(4-chloro-phenylamino)-5-amino-1,2,4-oxadiazole
3-(3,4-dichloro-phenylamino)-5-amino-1,2,4-oxadiazole
3-(2,3-dimethyl-phenylamino)-5-amino-1,2,4-oxadiazole
3-(2,3-dichloro-phenylamino)-5-amino-1,2,4-oxadiazole
3-(2-methyl-phenylamino)-5-amino-1,2,4-oxadiazole
3-(4-fluor-phenylamino)-5-amino-1,2,4-oxadiazole
3-(2,6-dichloro-phenylamino)-5-amino-1,2,4-oxadiazole
3-(2-chloro-phenylamino)-5-amino-1,2,4-oxadiazole
3-(4-chloro-phenylamino)-5-methylamino-1,2,4-oxadiazole
3-(2-chloro-phenylamino)-5-methylamino-1,2,4-oxadiazole
3-(3,4-dichloro-phenylamino)-5-methylamino-1,2,4-oxadiazole
3-(2,6-dichloro-phenylamino)-5-methylamino-1,2,4-oxadiazole.

Certain relevant compounds have been described in the literature (Helvetica Chimica Acta 63 (1980), 832 and 841) and are expressly excluded from the scope of the present invention.

Preferred acyl groups represented by $R^3$ are those having 1 to 4 carbon atoms. The alkyl groups may be linear or branched. Preferred are alkyl carbonyl groups having 1-3 carbon atoms in the alkyl group and the formyl group.

It has been found that those compounds of the present invention wherein $R^1$ and $R^2$ are methyl, fluorine, chlorine, or bromine are of particular effectiveness. Preferred are those compounds wherein $R^1$ and $R^2$ are chlorine. It is advantageous to have the substituents in the 2,6 or 2,3 position. $R^3$ is preferably hydrogen or acetyl and $R^4$ and $R^5$ are preferably hydrogen, methyl, or ethyl.

Another preferred group of compounds is that in which —X—Y— is —O—N—, and $R^1$ and $R^2$ are methyl, ethyl, and/or halogen. More preferably, $R^1$ and $R^2$ are bromine and/or chlorine and are located in the 2,3 position and especially in the 2,6 position.

Also of particular usefulness are those compounds wherein —X—Y— is —O—N—, and, when $R^1$ is a 4-methyl group, at least one of the remaining substituents is not hydrogen.

Also worthy of particular mention are those compounds wherein —X—Y— is —S—N—, $R^1$ and $R^2$ are methyl, ethyl, or halogen. Preferably, $R^1$ and $R^2$ are bromine and/or chlorine, and are located in the 2,3 position, especially the 2,6 position.

The compounds of the present invention, and their acid addition salts, have valuable therapeutic properties. They exhibit a strong bradycardiac effect. In particular they also evidence a strong long lasting hypotensive action. As a result, they can be used for the treatment of hypertension. The compounds can be administered orally or parenterally. A dose of 1.0 to 10.0 mg/kg, given orally, causes a long lasting reduction in blood pressure in renal or genetically hypertensive rats. The dosage in man is 0.5 to 30 mg/day.

Particularly preferred compounds are
3-amino-5-(2-chloro-3-bromo-phenylamino)-1,2,4-oxadiazole
3-amino-5-(2-bromo-3-chlorophenylamino)-1,2,4-oxadiazole
3-amino-5-(2-chloro-4-methyl-phenylamino)-1,2,4-oxadiazole
3-amino-5-(2-chloro-6-methyl-phenylamino)-1,2,4-oxadiazole
3-amino-5-(2-chloro-3-methyl-phenylamino)-1,2,4-oxadiazole
3-amino-5-(2,6-dibromo-phenylamino)-1,2,4-oxadiazole
3-amino-5-(2,4-dimethyl-phenylamino)-1,2,4-oxadiazole
3-methylamino-5-(2,6-dichloro-phenylamino)-1,2,4-oxadiazole
3-dimethylamino-5-(2,6-dichlorophenylamino)-1,2,4-oxadiazole
3-amino-5-(2-chloro-4-methyl-phenylamino)-1,2,4-thiadiazole
3-amino-5-(2-chloro-6-methyl-phenylamino)-1,2,4-thiadiazole
3-dimethylamino-5-(2,6-dichlorophenylamino)-1,2,4-thiadiazole
3-dibutylamino-5-(2,6-dichlorophenylamino)-1,2,4-thiadiazole
3-dibutylamino-5-(2,6-dichlorophenylamino)-1,2,4-oxadiazole
3-propylamino-5-(2,6-dichlorophenylamino)-1,2,4-oxadiazole A particularly preferred compound is 3-amino-5-(2,6-dichlorophenylamino)-1,2,4-oxadiazole.

The invention also includes pharmaceutical compositions which contain, as an active ingredient, a compound of Formula I together with a pharmaceutically acceptable carrier, diluent, or vehicle. The compounds can be mixed with the usual adjuvants, and can be administered in the usual manner; for example, orally or parenterally. The compounds can be provided in any of the usual forms as is customary and known to the person of ordinary skill. If prolongation of the effect of a dose is desired, the compounds of the present invention may be provided in time-delay form. Pharmaceutical preparations can advantageously contain the active ingredient in an amount of from 0.1 to 90%, particularly from 1.0 to 90%. The remainder is usually a vehicle or additive.

From the point of view of production and administration, solid preparations, such as tablets and capsules, are to be preferred. Such compositions may usefully contain the active ingredient in amounts of from 0.25 to 30 mg for the treatment of hypertension.

The compounds of the present invention can be prepared in accordance with the following methods, each of which are applicable to certain groups of such compounds.

To prepare compounds wherein X is oxygen and R³ is hydrogen, dichlorides of the formula

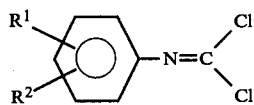

are cyclized, in the presence of a base, with a hydroxyguanidine of the formula

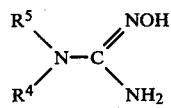

The preferred bases are sodium hydroxide and calcium hydroxide, especially where dioxane-water mixtures are used as solvents. The substituted hydroxyguanidines can also be used in the form of their acid addition salts. The above-mentioned dichlorides and guanidines used as starting materials in the aforementioned process are known or obtainable according to known methods.

The compounds wherein X is sulfur and R³ is hydrogen are produced by oxidative cylization of thioureas of the formula

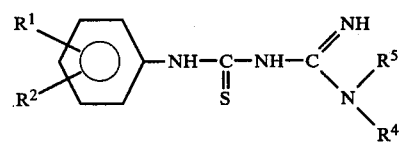

Suitable oxidants are N-halogen succinimides, tert.-butylhypochlorite, alkali-hypohalides, and hydrogen peroxide. The reaction is carried out at temperatures between 20° and 100° C.

The thioureas used as starting materials in this process are obtained by the known reaction of phenyl-substituted isothiocyanates with guanidine or alkyl-substituted guanidines. These compounds are known per se or are obtainable according to known methods.

Both the oxadiazoles and the thiadiazoles wherein R³ is acyl are obtained by reacting the corresponding compounds in which R³ is hydrogen with acyl halides or acid anhydrides in the presence of organic bases, preferably pyridine.

The oxadiazoles and thiadiazoles of the present invention, wherein R³ is an alkyl group or alkenyl group, may be obtained by reacting the compound wherein R³ is hydrogen with alkyl halides or alkenyl halides and bases. The preferred bases are alkali alcoholates coupled with the use of the corresponding alcohols as solvents.

The oxadiazoles wherein X is nitrogen, Y is oxygen, and R³ is hydrogen, are obtained by reacting guanidines of the formula

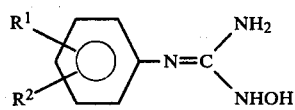

with trichloroacetanhydride, preferably in the presence of trichloroacetic acid. This forms diazoles of the formula

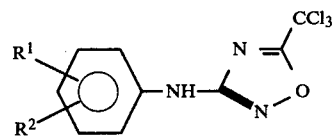

the compounds of the foregoing formula can be reacted with ammonia or with amines of the formula

and the splitting off of the trichloromethyl group produces the desired compounds. The reaction takes place preferably in an alcohol solution at 20° to 60° C.

The compounds of formula V can be obtained by reacting thioureas of the formula

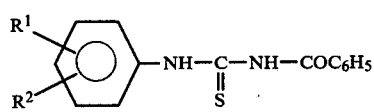

with an amine of the formula

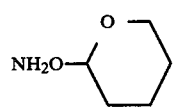

in the presence of mercuric oxide or lead oxide to form compounds of the formula

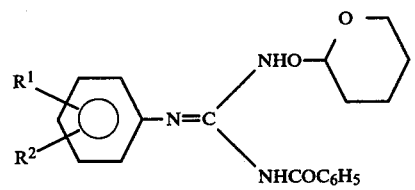

These compounds are subjected to alkaline hydrolysis and separation of the benzoyl radical, followed by acid hydrolysis to produce the compounds of formula V. The compounds of formulas VII and VIII are known as such or obtainable in accordance with known methods.

The following examples are intended to illustrate the present invention.

EXAMPLE 1

3-amino-5-(2,6-dichlorophenylamino)-1,2,4-oxadiazole 39.2 (0.16 mole) 2,6-dichlorophenyl-isocyanide dichloride in 270 ml dioxane are added in drops at 20° C. to a solution of 20 g (0.16 mole) hydroxyguanidine sulfate in 240 ml 2-N soda lye. After 15 hours, the dioxane is distilled off under vacuum, and the aqueous phase is extracted with methylene chloride. After column-chromatography on silica gel, 4.5 g 3-amino-5-(2,6-dichlorophenyl amino)-1,2,4-oxadiazole having a melting point of 180°–181° C., is obtained.

The compounds of the formula I listed in the following table are prepared by analogy to Example 1:

| Example No. | $R^1$ | $R^2$ | $R^3$ | $R^4$ | $R^5$ | X | Mp. °C. |
|---|---|---|---|---|---|---|---|
| 2 | 2-$CH_3$ | 6-$CH_3$ | H | H | H | O | 151–152 |
| 3 | 3-Cl | 4-Cl | H | H | H | O | 153–154 (decomp) |
| 4 | 2-$CH_3$ | 5-F | H | H | H | O | 162–164 |
| 5 | 2-$CH_3$ | 4-Cl | H | H | H | O | 186–188 (decomp) |
| 6 | 2-Cl | 3-Cl | H | H | H | O | 148–149 |
| 7 | 2-Br | 3-Br | H | H | H | O | 187–188 |

EXAMPLE 8

3-amino-5-(2,6-dimethylphenylamino)-1,2,4-thiadiazole

A solution of 7.0 g (0.03 mole) 1-amidino-3-(2,6-dimethylphenyl)-thiourea in 150 ml methylene chloride is stirred with 4.2 g (0.03 mole) N-chlorosuccinimide (95%) for 1 hour at 20° C., then for another hour after the addition of 15 ml conc. NaOH. After dilution with water, the methylene chloride phase is separated by filtration and, by column-chromatography with silica gel (MeOH/$CHCl_3$: 10/90), 4.8 g 3-amino-5-(2,6-dimethylphenylamino)-1,2,4-thiadiazole having a melting point of 180° C. is obtained.

EXAMPLE 9

3-amino-5-(2,6-dichlorophenylamino)-1,2,4-thiadiazole

To a solution of 4 g 1-aminidino-3-(2,6-dichlorophenyl)thiourea in 35 ml ethanol are added in drops 26 ml 6% $H_2O_2$ after addition of 1.7 ml conc. hydrochloric acid at boiling temperature. After evaporation of the ethanol, the residue is suspended in sodium hydrogen carbonate solution, filtered, and washed with water. 2.8 g 3-amino-5-(2,6-dichlorophenylamino)-1,2,4-thiadiazole having a melting point of 178°–179° C. is obtained.

In a manner analogous to Examples 8 and 9, the following compounds are synthesized.

EXAMPLE 10

3-amino-5-(2,3-dichlorophenylamino)-1,2,4-thiadiazole

Mp. 161°–163° C.

EXAMPLE 11

3-amino-5-(2,6-dibromophenylamino)-1,2,4-thiadiazole

Mp. 224°–227° C.

The amidinothioureas used for the preparation of the 1,2,4-thiadiazoles are new compounds and can be synthesized as described in Example 12.

EXAMPLE 12

1-amidino-3-(2,6-dichlorophenyl)-thiourea 12 g (0.06 mole) 2,6-dichlorophenylisothiocyanate in 100 ml dimethoxyethane are mixed with 5.4 g (0.09 mole) guanidine and stirred for 1 hour at 25° C. After evaporation of the solvent, the residue is recrystallized from ethanol.

Yield: 6.4 g. Mp. 189°–190° C.

The following compounds were prepared in a manner analogous to that of Example 12.

1-amidino-3-(2,6-dimethylphenyl)-thiourea, mp. 154°–156° C.

1-amidino-3-(2,3-dichlorophenyl)-thiourea, mp. 150°–152° C.

1-amidino-3-(2,6-dibromophenyl)-thiourea, mp. 220°–222° C.

EXAMPLE 13

3-amino-5-[N-acetyl-N-(2,6-dichlorophenyl)-amino]-1,2,4-oxadiazole 2.4 g (0.01 mole) 3-amino-5-(2,6-dichlorophenylamino)-1,2,4-oxadiazole in 10 ml pyridine are mixed with 5 moles acetanhydride at room temperature and stirred for 2 hours at 25°–30° C. After evaporation of the solvent, the residue is taken up at $CHCl_3$ and shaken with sodium hydrogen carbonate solution. The $CHCl_3$ phase contains 3 g of the N-acetyl compound, which is purified by column-chromatography on silica gel. The product has a melting point of 164°–165° C.

EXAMPLE 14

3-amino-5-[N-(2,6-dichlorophenyl)-N-methyl-amino]-1,2,4-oxadiazole 3.0 g (0.012 mole) 3-amino-5-(2,6-dichlorophenylamino)-1,2,4-oxadiazole were added to a solution of 0.6 g (0.025 mole) sodium in 100 ml methanol, and 1.6 ml (0.024 mole) methyl iodide are added in drops and stirred for 24 hours at room temperature. The solvent is distilled off under vacuum, the residue taken up in methylene chloride, extracted with water and, after evaporation of the solvent, 2.8 g of the N-methyl compound, which has an mp. of 177°–178° C. after recrystallization from acetic ester/diisopropyl ether is obtained.

By analogy to Example 14, the following compounds are obtained from the corresponding compounds in which $R^3$ denotes a hydrogen atom.

| Example | $R^1$ | $R^2$ | $R^3$ | $R^4$ | $R^5$ | X | mp. °C. |
|---|---|---|---|---|---|---|---|
| 15 | 2-Cl | 6-Cl | $(CH_3)_2CH-$ | H | H | O | 175–177 |
| 16 | 2-Cl | 6-Cl | $CH_3(CH_2)_3-$ | H | H | O | 126–127 |
| 17 | 2-Cl | 6-Cl | $-CH_2CH=CH_2$ | H | H | O | 143–144 |
| 18 | 2-Cl | 6-Cl | $-CH_3$ | H | H | S | 181–182 |

EXAMPLE 19

3-(2,6-dichlorophenylamino)-5-dimethyl-amino-1,2,4-oxadiazole (a) 40.0 g 1-(2,6-dichlorophenyl)-3-benzoyl-thiourea and 31.6 g tetrahydropyran-2-yl-oxyamine are dissolved in 700 ml methylene chloride and stirred vigorously for several hours at 20° C. after the addition of freshly precipitated mercury (II)-oxide (from 73.3 g $HgCl_2$ and 32.4 g NaOH) in aqueous suspension. The suspension is filtered over cellulose powder, and the mercury sulfide is removed. The organic phase is separated and evaporated. The residue is then washed with ether and filtered.

Yield: 38.5 g 1-(2,6-dichlorophenyl)-2-benzoyl-3-tetrahydropyranyloxyguanidine.
Mp. 150°-151° C.

The following compound is prepared in a similar manner.

1-(2,6-dimethylphenyl)-2-benzoyl-3-tetrahydropyranyloxyguanidine.
Mp: formed an oil.

(b) 38.5 g 1-(2,6-dichlorophenyl)-2-benzoyl-3-tetrahydropyranyloxyguanidine are heated to a boil with 900 ml 5% NaOH (in a mixture water/ethanol 1:1) for 2 hours. After cooling, 25.1 g 1-(2,6-dichlorophenyl)-2-tetrahydropyranyloxyguanidine having a melting point of 178°-180° C. is obtained.

The following compound is prepared in a similar manner.

1-(2,6-dimethylphenyl)-2-tetrahydropyranyloxyguanidine. Mp. 108°-109° C.

(c) 17.2 g 1-(2,6-dichlorophenyl)-2-tetrahydropyranyloxyguanidine are hydrolyzed with 150 ml ethanolic hydrochloric acid for 15 hours at room temperature. After evaporation of the ethanol, the residue is dissolved in water, neutralized with 2-N NaOH, and extracted with methylene chloride. 10.2 g 1-(2,6-dichlorophenyl)-2-hydroxyguanidine having a melting point of 113° C. (decomp.) is obtained.

The following compound is prepared in a similar manner. 1-(2,6-dimethylphenyl)-2-hydroxy-guanidine. Mp 140°-141° C.

(d) 3.0 g 1-(2,6-dichlorophenyl)-2-hydroxy-guanidine are heated in 2.7 g trichloroacetic acid and 8.6 g trichloroacetic anhydride for 1 hour at 110° C. After cooling, the mixture is poured over ice water and extracted with chloroform. After recrystallization from isopropanol, 3.1 g 3-(2,6-dichlorophenylamino)-5-trichloromethyl-1,2,4-oxadiazole having a melting point of 163° to 164° C. are obtained.

The following compound is obtained in a similar manner:

3-(2,6-dimethylphenylamino)-5-trichloromethyl-1,2,4-oxadiazole, Mp. 100°-101° C.

(e) 3.1 g 3-(2,6-dichlorophenylamino)-5-trichloromethyl-1,2,4-oxadiazole are dissolved in 20 ml ethanol and heated with 20 ml aqueous dimethylamine solution (34%) in an autoclave for 3 hours at 50° C. After recrystallization from methanol/diisopropyl ether, 1.5 g 3-(2,6-dichlorophenylamino)-5-dimethylamino-1,2,4-oxadiazole having a melting point of 196°-197° C. is obtained.

The compounds listed in the following table are prepared by analogy to Example 19.

| Example | $R^1$ | $R^2$ | $R^4$ | $R^5$ | X | Y | mp °C. |
|---|---|---|---|---|---|---|---|
| 20 | 2-Cl | 6-Cl | H | $C_4H_9$ | N | O | 133-134 |
| 21 | 2-$CH_3$ | 6-$CH_3$ | H | H | N | O | 195-198 (decomp) |

EXAMPLE 22

Manufacture of tablets

Tablets which contain the ingredients listed below can be manufactured in known manner. They can be used for the treatment of hypertension in a dose of 1 to 2 tablets twice a day.

| | |
|---|---|
| 3-amino-5-(2,6-dichlorophenylamino)-1,2,4-oxadiazole | 0.25 mg |
| lactose | 75 mg |
| corn starch | 10 mg |
| microcrystalline cellulose | 8 mg |
| polyvinyl pyrrolidone | 1 mg |
| magnesium stearate | 0.5 mg |
| highly dispersed silicon dioxide | 0.5 mg |

While only a limited number of specific embodiments of the present invention have been expressly disclosed, it is, nonetheless, to be broadly construed, and not to be limited except by the character of the claims appended hereto.

What we claim is:

1. A method of treating hypertension comprising administering to a warm-blooded animal an effective amount of a compound of the formula

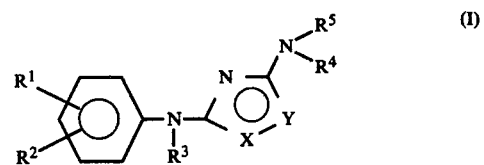

wherein $R^1$ is hydrogen, halogen, or alkyl, $R^2$ is halogen or alkyl, $R^3$ is hydrogen, alkanoyl, or aliphatic, $R^4$ and $R^5$ are individually hydrogen or alkyl, wherein said alkyl and said alkanoyl are branched or straight chain and each contains 1 to 4 carbon atoms, X is oxygen, nitrogen or sulfur, Y is oxygen or nitrogen, and —X—Y— is —O—N—, —N—O—, or —S—N—, and pharmaceutically acceptable acid addition salts thereof, except 3-amino-5-(4-methyl-phenylamino)-1,2,4-oxadiazole,
3-(4-methyl-phenylamino)-5-amino-1,2,4-oxadiazole
3-(4-chloro-phenylamino)-5-amino-1,2,4-oxadiazole
3-(3,4-dichloro-phenylamino)-5-amino-1,2,4-oxadiazole
3-(2,3-dimethyl-phenylamino)-5-amino-1,2,4-oxadiazole
3-(2,3-dichloro-phenylamino)-5-amino-1,2,4-oxadiazole
3-(2-methyl-phenylamino)-5-amino-1,2,4-oxadiazole
3-(4-fluor-phenylamino)-5-amino-1,2,4-oxadiazole
3-(2,6-dichloro-phenylamino)-5-amino-1,2,4-oxadiazole
3-(2-chloro-phenylamino)-5-amino-1,2,4-oxadiazole
3-(4-chloro-phenylamino)-5-methylamino-1,2,4-oxadiazole
3-(2-chloro-phenylamino)-5-methylamino-1,2,4-oxadiazole
3-(3,4-dichloro-phenylamino)-5-methylamino-1,2,4-oxadiazole
3-(2,6-dichloro-phenylamino)-5-methylamino-1,2,4-oxadiazole.

2. The method of claim 1 wherein said amount is 0.25 to 30 mg per day per person.

3. The method of claim 1 wherein $R^3$ is an unsaturated aliphatic.

4. The method of claim 1 wherein said compound is administered as part of a pharmaceutical composition comprising said compound and a pharmaceutically acceptable carrier.

5. The method of claim 1 wherein $R^1$ and $R^2$ are individually methyl, fluorine, chlorine, or bromine.

6. The method of claim 1 wherein $R^1$ and $R^2$ are chlorine.

7. The method of claim 1 wherein $R^1$ and $R^2$ are in the 2,6 or 2,3 position.

8. The method of claim 1 wherein $R^3$ is hydrogen or acetyl.

9. The method of claim 1 wherein $R^4$ and $R^5$ are individually hydrogen, methyl, or ethyl.

10. The method of claim 1 wherein —X—Y— is —O—N— and $R^1$ and $R^2$ are individually methyl, ethyl, or halogen.

11. The method of claim 6 wherein $R^1$ and $R^2$ are individually bromine or chlorine.

12. A compound of claim 6 or 7 wherein $R^1$ and $R^2$ are in the 2,3 position.

13. The method of claim 6 or 7 wherein $R^1$ and $R^2$ are in the 2,6 position.

14. The method of claim 1 wherein —X—Y— is —O—N— and, when $R^1$ is 4-methyl, at least one of the remaining substituents is not hydrogen.

15. The method of claim 1 wherein —X—Y— is —S—N— and $R^1$ and $R^2$ are individually methyl, ethyl, or halogen.

16. The method of claim 11 wherein $R^1$ and $R^2$ are individually bromine or chlorine.

17. The method of claim 11 or 12 wherein $R^1$ and $R^2$ are in the 2,3 position.

18. The method of claim 11 or 12 wherein $R^1$ and $R^2$ are in the 2,6 position.

19. The method of claim 1 wherein said compound is taken from the class consisting of 3-amino-5-(2-chloro-3-bromo-phenylamino)-1,2,4-oxadiazole 3-amino-5-(2-bromo-3-chlorophenylamino)-1,2,4-oxadiazole 3-amino-5-(2-chloro-4-methyl-phenylamino)-1,2,4-oxadiazole 3-amino-5-(2-chloro-6-methyl-phenylamino)-1,2,4-oxadiazole 3-amino-5-(2-chloro-3-methyl-phenylamino)-1,2,4-oxadiazole 3-amino-5-(2,6-dibromo-phenylamino)-1,2,4-oxadiazole 3-amino-5-(2,4-dimethyl-phenylamino)-1,2,4-oxadiazole 3-methylamino-5-(2,6-dichloro-phenylamino)-1,2,4-oxadiazole 3-dimethylamino-5-(2,6-dichlorophenylamino)-1,2,4-oxadiazole 3-amino-5-(2-chloro-4-methyl-phenylamino)-1,2,4-thiadiazole 3-amino-5-(2-chloro-6-methyl-phenylamino)-1,2,4-thiadiazole 3-dimethylamino-5-(2,6-dichlorophenylamino)-1,2,4-thiadiazole 3-dibutylamino-5-(2,6-dichlorophenylamino)-1,2,4-thiadiazole 3-dibutylamino-5-(2,6-dichlorophenylamino)-1,2,4-oxadiazole 3-propylamino-5-(2,6-dichlorophenylamino)-1,2,4-oxadiazole 20. The method of claim 32 wherein said compound is 3-amino-5-(2,6-dichlorophenylamino)-1,2,4-oxadiazole.

21. The method of claim 1 wherein —X—Y— is —O—N—.

22. The method of claim 1 wherein —X—Y— is —N—O—.

23. The method of claim 1 wherein —X—Y— is —S—N—.

* * * * *